United States Patent
Okutani et al.

(10) Patent No.: US 8,642,070 B2
(45) Date of Patent: Feb. 4, 2014

(54) FEED ADDITIVE COMPOSITION FOR RUMINANTS, AND FEED CONTAINING THE SAME, AND METHOD OF FABRICATING SUCH FEED ADDITIVE COMPOSITION FOR RUMINANTS

(75) Inventors: Akira Okutani, Anan (JP); Hiroaki Motoki, Anan (JP); Eiji Tamura, Anan (JP); Yumi Takashima, Anan (JP); Shunsuke Sakai, Anan (JP)

(73) Assignee: Bio Science Co., Ltd., Tokushima (JP)

( * ) Notice: Subject to any disclaimer, the term of this patent is extended or adjusted under 35 U.S.C. 154(b) by 2064 days.

(21) Appl. No.: 10/588,969

(22) PCT Filed: Apr. 27, 2005

(86) PCT No.: PCT/JP2005/008074
§ 371 (c)(1),
(2), (4) Date: Aug. 10, 2006

(87) PCT Pub. No.: WO2005/104868
PCT Pub. Date: Nov. 10, 2005

(65) Prior Publication Data
US 2007/0148212 A1    Jun. 28, 2007

(30) Foreign Application Priority Data

Apr. 30, 2004 (JP) ................. 2004-135276
Nov. 19, 2004 (JP) ................. 2004-335286

(51) Int. Cl.
*A23K 1/17* (2006.01)
*A23K 1/165* (2006.01)

(52) U.S. Cl.
USPC ........................................ 424/442

(58) Field of Classification Search
USPC ........................................ 424/442
See application file for complete search history.

(56) References Cited

U.S. PATENT DOCUMENTS

| | | | |
|---|---|---|---|
| 4,770,876 A | * | 9/1988 | Bischoff et al. ............... 424/119 |
| 5,676,966 A | * | 10/1997 | Kitamura et al. ............. 424/438 |
| 6,475,510 B1 | * | 11/2002 | Venkatesh et al. ............ 424/441 |

FOREIGN PATENT DOCUMENTS

| | | |
|---|---|---|
| JP | 57-047466 | 3/1982 |
| JP | 58-175449 | 10/1983 |
| JP | 60-168351 | 8/1985 |
| JP | 63-317053 | 12/1988 |
| JP | 05-023114 | 2/1993 |
| JP | 06-237702 | 8/1994 |
| JP | 06-276957 | 10/1994 |
| JP | 07-067547 | 3/1995 |
| JP | 07-289172 | 11/1995 |
| JP | 09-187228 | 7/1997 |
| JP | 10-215789 | 8/1998 |
| JP | 2000-060440 | 2/2000 |
| JP | 2002-500659 | 1/2002 |
| WO | 94/06307 | 3/1994 |
| WO | 98/53907 | 12/1998 |

* cited by examiner

*Primary Examiner* — Benjamin Packard
(74) *Attorney, Agent, or Firm* — Wenderoth, Lind & Ponack, L.L.P.

(57) ABSTRACT

The coating composition which coats the biologically active substance includes at least one protective material selected from the group consisting of a hardened animal fat, a hardened vegetable oil, a linear or branched, saturated or unsaturated aliphatic monocarboxylic acid having 12 to 22 carbon atoms, a fatty acid ester, and a wax group; lecithin; and at least one preservative selected from a propionic acid or its salt, a sorbic acid or its salt, a benzoic acid or its salt, a dehydroacetic acid or its salt, parahydroxybenzoic acid esters, an imazalil, a thiabendazole, an orthophenyl phenol, an orthophenyl phenol natrium, and a diphenyl.

12 Claims, 2 Drawing Sheets

FEED ADDITIVE COMPOSITION FOR RUMINANTS, AND FEED CONTAINING THE SAME, AND METHOD OF FABRICATING SUCH FEED ADDITIVE COMPOSITION FOR RUMINANTS

TECHNICAL FIELD

The present invention relates to a feed additive composition for ruminants such as a rumen bypass product etc. for ruminants, feed containing such feed additive composition for ruminants, and a method of fabricating such feed additive composition for ruminants. More particularly, the invention relates to a rumen bypass product and the like for ruminants, in which a biologically active substance is coated with a coating composition which enables the substance to be stably protected within the first stomach compartment (i.e., the rumen) of ruminants and to be released in the abomasum and/or the subsequent digestive tract, for easier digestion and absorption of the biologically active substance in the abomasum and/or the subsequent digestive tract.

BACKGROUND ART

Unlike a monogastric animal such as a human and others, a ruminant animal such as cattle etc. has a plurality of stomach compartments, with the first compartment (i.e., the rumen) being resided by a large population of microorganisms. A natural process is called a rumination when rumen contents are regurgitated to the mouth, and then salivated, masticated, and swallowed back. In view of such rumination, when a biologically active substance contained in feed without any pre-treatment is orally administered to ruminants, a majority of such substance will only be attacked and broken down by the rumen microorganisms. For example, when a biologically active substance such as a vitamin, an amino acid, and the like is administered to cattle, most of the substance is attacked and broken down by the microorganisms residing in the rumen, resulting in loss without effective digestion and absorption. When the biologically active substance is prepared in the form of a rumen bypass product to be protected from attack and breakdown by the rumen microorganisms for effective digestion and absorption in the abomasal and postabomasal digestive tract (i.e., the abomasum and the small intestine), such biologically active substance can serve as a very useful nutrient agent etc.

Conventionally, rumen bypass products have long been utilized, by dispersing a biologically active substance in a protective material such as wax, animal and vegetable fats and oils or their hardened materials, or by coating a core which contains a biologically active substance. For example, methods of dispersing a biologically active substance in a protective material have been developed, such as a method of granulating through blending a biologically active substance with a protective material (refer to Unexamined Japanese Patent Application (Kokai) No. 1985-168351 (Patent Reference 1)), or a method of granulating through melting, in which a melt liquid with a biologically active substance being blended and suspended in a molten protective material is dropped onto a belt (refer to Unexamined Japanese Patent Application (Kokai) No. 1983-175449 (Patent Reference 2)).

Alternatively, by way of coating a biologically active substance with a protective material, there is a method developed for forming a core that contains a biologically active substance and then coating the core with a protective material (refer to Unexamined Japanese Patent Application (Kokai) Nos. 1988-317053 and 1993-23114 (Patent Reference 3 and 4)).

DISCLOSURE OF THE INVENTION

However, a rumen bypass product fabricated by a method of dispersing a biologically active substance faces a problem that a sufficient rumen bypass effect is not exhibited in the case of a biologically active substance having a higher water solubility. Also, in the case of a rumen bypass product fabricated by a method of coating a biologically active substance with a protective material, while exhibiting a performance required of a rumen bypass product, its fabrication process is complicated, with a resultant problem of a higher cost of manufacture, because this process involves a plurality of steps, such as 1) a core formation step (a granule granulated through extrusion is further to be prepared into a spherical granule), and 2) a coating step (the core is to be coated). Particularly in this granulation through extrusion, an extrusion under elevated temperature and pressure can lead to a biologically active substance, such as a thermally vulnerable vitamin, being disintegrated, and a fabricating apparatus is expensive as well. In addition, a granulated rumen bypass product available from the granulation through extrusion is generally provided in a cylindrical or prismatic form, having an edge portion where the biologically active substance may not be fully coated. When a granule has an incompletely coated portion, the biologically active substance is prone to be eluted, being unable to satisfactorily perform as required of a rumen bypass product. Furthermore, a granule having a jut such as an edge is prone to be abraded by the ruminal inner wall of ruminants like cattle, inviting a problem that a peeled coating is liable to allow a biologically active substance to be eluted.

On the other hand, since only a limited number of ingredients is available in a biologically active substance contained in a rumen bypass product, stockbreeders and other concerned parties have long been eager for such a rumen bypass product as may contain a greater variety of amino acids, vitamins, and the like.

With regard to a rumen bypass product being prepared by granulating through dispersing a biologically active substance in a protective material, the biologically active substance with a lower water solubility can be obtained as an effective rumen bypass product when the substance content is 40% or less. However, in the case of a biologically active substance such as a lysine hydrochloride which is of a higher water solubility, even a 40% or less content of the biologically active substance cannot be an effective rumen bypass product because of its lower rumen bypassing property.

Thus, while numerous proposals have been made regarding such a coating composition for a rumen bypass product for ruminants as stably protects a biologically active substance in the rumen of ruminants and facilitates releasability in the abomasum and/or the subsequent digestive tract, a rumen bypass product is generally still under study which has both a protective ability in the rumen and a releasability in the abomasum and/or the subsequent digestive tract. This is believed to be because an adequate study has not been made regarding an evaluation method of a protective ability in the rumen of ruminants, a particle size of a rumen bypass product, and a structure of a coating layer etc.

In Unexamined Japanese Patent Application (Kokai) Nos. 1993-23114 and 1997-187228 (Patent Reference Nos. 4 and 5) for example, a protective ability for a biologically active substance in the rumen is evaluated, being based only on a simulated ruminal fluid with an adjusted pH value and liquid temperature, in which a study is not given to any effects by microorganisms residing in the rumen which is a factor peculiar to ruminants such as cattle. In fact, while a high protective ability is exhibited when tested in a simulated ruminal fluid, a commercially available rumen bypass product is found to be failing in a protective ability to a large extent when the product is assayed using a real ruminal fluid of ruminants resided by microorganisms. This is believed to be resultant from the effects by a large population of microorganisms in the rumen of ruminants. As such, it will be necessary to take into account the effects from the large population of microorganisms in the rumen of ruminants, and coat a biologically active substance with a coating composition that can inhibit such effects.

In Unexamined Japanese Patent Application (Kokai) No. 2000-60440 (Patent Reference No. 6) as well, while a protective ability for a rumen bypass product is assayed, being based on a ruminal fluid resided by microorganisms, the product has disadvantages that a preparation ranging in a larger particle size of 4 to 15 mm can lead to an easy break by mastication, and that duplex coatings on the rumen bypass product are likely to extremely reduce the protective ability when the coatings on the core surface are damaged by a rumination, mastication, etc.

As can be seen from the above description, in those rumen bypass products currently available in the market, it may be well said that they have not reached a fully satisfactory level in terms of protective ability for a biologically active substance in the rumen resided by microorganisms. The cause is resultant from the effects by the microorganisms residing in the rumen which are peculiar to ruminants, and thus it is required that a protective ability in the rumen be studied with a due consideration of the presence of such microorganisms. Those microorganisms residing in the rumen of the ruminants, on the other hand, serve as a source of essential energy for maintaining the life of ruminants, and such microorganisms can be a source of nutrients such as proteins, etc. As such, it is required that a rumen bypass product for ruminants be developed which is coated with a coating composition so that the biologically active substance may be protected without affecting the life of ruminal microorganisms.

The present invention has been made in view of the above-described circumstances. The principal object of the invention is to provide a feed additive composition for ruminants which is excellent in a rumen bypassing property of a biologically active substance even when a highly water-soluble biologically active substance is contained in a preparation where the biologically active substance is granulated through being dispersed in a protective material, and which is also excellent in releasability in the abomasum and/or the subsequent digestive tract, and also to provide feed containing such a feed additive composition for ruminants as well as a method of fabricating such feed additive composition for ruminants. Another object of the invention is to provide a feed additive composition for ruminants which can stably protect a biologically active substance in the rumen of ruminants resided by microorganisms and which can be fabricated at a lower cost, and to provide feed containing such feed additive composition for ruminants as well as a method of fabricating such feed additive composition for ruminants.

In order to achieve the above-described objects, the feed additive composition for ruminants in accordance with a first aspect of the present invention is a feed additive composition for ruminants which has a biologically active substance coated with a coating composition, in which the coating composition includes at least one protective material selected from the group consisting of a hardened animal fat, a hardened vegetable oil, a linear or branched, saturated or unsaturated aliphatic monocarboxylic acid having 12 to 22 carbon atoms, a fatty acid ester, and a wax group; lecithin; and at least one preservative selected from a propionic acid or its salt, a sorbic acid or its salt, a benzoic acid or its salt, a dehydroacetic acid or its salt, parahydroxybenzoic acid esters, an imazalil, a thiabendazole, an orthophenyl phenol, an orthophenyl phenol natrium, and a diphenyl. This combination enables a protective ability (a rumen bypass ratio) in the rumen of ruminants to be improved. Also, in the case of a preparation granulated through dispersing a biologically active substance in the protective material, the biologically active substances, particularly a lysine hydrochloride, a betaine, a taurine and/or a highly water-soluble biologically active substance such as a water-soluble vitamin, can also be formed into a rumen bypass product that is excellent in digestion and absorption.

In accordance with a second aspect of the present invention, the preservative content of the feed additive composition for ruminants is in a range of from 0.01 to 2.0% by weight.

In accordance with a third aspect of the present invention, the preservative contained in the feed additive composition for ruminants is a propionic acid or its salt.

In accordance with a fourth aspect of the present invention, the biologically active substance in the feed additive composition for ruminants contains at least a lysine hydrochloride.

In accordance with a fifth aspect of the present invention, the protective material in the feed additive composition for ruminants contains at least a linear or branched, saturated or unsaturated aliphatic monocarboxylic acid having 12 to 22 carbon atoms.

In accordance with a sixth aspect of the present invention, the linear or branched, saturated or unsaturated aliphatic monocarboxylic acid having 12 to 22 carbon atoms contained in the feed additive composition for ruminants, is a stearic acid.

In accordance with a seventh aspect of the present invention, a mean particle size of the biologically active substance, contained in the feed additive composition for ruminants, is in a range of from 1 to 150 µm.

In accordance with an eighth aspect of the present invention, the lecithin content of the feed additive composition for ruminants is in a range of from 0.1 to 10.0% by weight.

In accordance with a ninth aspect of the present invention, the biologically active substance content of the feed additive composition for ruminants is in a range of from 1 to 50% by weight.

In accordance with a tenth aspect of the present invention, the feed additive composition for ruminants is obtained by: dispersing and/or dissolving the biologically active substance in a melt blending liquid constituting the coating composition, for producing an injection melt liquid; and granulating through injecting the injection melt liquid into air.

In accordance with an eleventh aspect of the present invention, the feed additive composition for ruminants obtained by granulation through injection is in a spherical form. With this structure, a feed additive composition for ruminants can be obtained which is coated with a stable coating composition and which is less likely to be eluted in the rumen.

In accordance with a twelfth aspect of the present invention, the feed contains the above-described feed additive composition.

In the method in accordance with a thirteenth aspect of the present invention, the feed additive composition for ruminants is fabricated by 1) preparing a melt liquid constituting a protective material, adjusted at 50 to 90° C., the melt liquid containing: at least one substance selected from the group consisting of a hardened animal fat, a hardened vegetable oil, and a wax group; lecithin; and a linear or branched, saturated or unsaturated aliphatic monocarboxylic acid or its salt having 12 to 22 carbon atoms, individually or in a mixture of two or more; 2) dispersing and/or dissolving a biologically active substance in the melt liquid, for producing an injection melt liquid; and 3) granulating through injecting the injection melt liquid into air at liquid temperature of from 50 to 90° C. With this method, an extremely effective feed additive composition for ruminants can be provided as a rumen bypass product available at a lower price.

Furthermore, in the method of fabricating a feed additive composition for ruminants in accordance with a fourteenth aspect of the present invention, a linear or branched, saturated or unsaturated aliphatic monocarboxylic acid or its salt having 12 to 22 carbon atoms is a stearic acid.

Furthermore, in the method of fabricating a feed additive composition for ruminants in accordance with a fifteenth aspect of the present invention, the feed additive composition contains at least a taurine and/or a betaine, to constitute a biologically active substance.

Furthermore, in the method of fabricating a feed additive composition for ruminants in accordance with a sixteenth aspect of the present invention, the feed additive composition is further blended with at least one selected from the group consisting of a propionic acid or its salt, a sorbic acid or its salt, a benzoic acid or its salt, a dehydroacetic acid or its salt, paraoxybenzoic esters, an imazalil, a thiabendazole, an orthophenyl phenol, an orthophenyl phenol natrium, and a diphenyl, to constitute a preservative.

In accordance with the inventive feed additive composition for ruminants, the feed containing such feed additive composition for ruminants, and the inventive method of fabricating the feed additive composition for ruminants, a rumen bypass product can be fabricated at a lower cost, which is excellent in protective ability in the rumen of ruminants and also in releasability in the abomasum and/or subsequent digestive tract. In particular, a rumen bypass product which is obtained by granulating through injecting a melt liquid of coating composition containing a biologically active substance can be an extremely good rumen bypass product in that a biologically active substance with a higher water solubility is less likely to be eluted in the rumen, and in that the biologically active substance is effectively released in the abomasum and/or the subsequent digestive tract. In addition, a fabrication of the rumen bypass product can be extremely simplified, so that the rumen bypass product is obtained simply by granulating through dissolving a melt liquid which has the biologically active substance dispersed in a dissolved coating composition, while a cost of manufacture can be reduced to minimum.

BEST MODE FOR CARRYING OUT THE INVENTION

Embodiments of the present invention will now be described. It should be noted, however, that the embodiments to be described below are merely illustrative of a feed additive composition for ruminants, feed containing the same, and a method of fabricating the feed additive composition for ruminants in order to embody the spirit of the present invention, and that the present invention is not limited to the feed additive composition for ruminants, the feed containing the same, and the method of fabricating the feed additive composition for ruminants that are described below. Also, in the present disclosure, those members described in the appended claims are, in no way, specified to the members described in the embodiments. Particularly, unless otherwise specifically set forth herein, the scope of the present invention is not contemplated to be limiting to but is rather intended to be merely illustrative of the components described in the embodiments, in terms of material quality, shape, and relative disposition thereof. It should also be added that each component constituting the present invention may be either realized in a manner of integrating a plurality of components into the same member to utilize such a member for a plurality of factors, or conversely, may be realized in a manner of sharing a plurality of members to perform a function of one member.

After making extensive studies, the present inventors have found that the preparation, which is obtained only by the granulation as enumerated herein, can serve as an extremely effective rumen bypass product and can be provided at a lower price, the granulation including the steps of: 1) preparing a melt liquid constituting a coating composition, adjusted at 50 to 90° C., the melt liquid containing: at least one substance selected from the group consisting of a hardened animal fat, a hardened vegetable oil, and a wax group; lecithin; and a linear or branched, saturated or unsaturated aliphatic monocarboxylic acid or its salt having 12 to 22 carbon atoms, individually or in a mixture of two or more; 2) dispersing and/or dissolving a biologically active substance in the melt liquid, for producing an injection melt liquid; and 3) granulating through injecting or spraying the injection melt liquid into air at liquid temperature of from 50 to 90° C.

As for granulation through melting, a method can be enumerated such as by granulating through freezing and solidifying a melt liquid in air, oil, water, or over a belt etc. The method of obtaining a granulated product of feed additive composition in accordance with the present embodiment includes the steps of: 1) melting a coating composition into a liquid containing: at least one substance selected from the group consisting of a hardened animal fat, a hardened vegetable oil, and a wax group; lecithin; and a linear or branched, saturated or unsaturated aliphatic monocarboxylic acid or its salt having 12 to 22 carbon atoms, individually or in a mixture of two or more; 2) preparing such a melt liquid to make up a melt liquid of coating composition kept warming at 50 to 90° C.; 3) uniformly blending and dispersing a biologically active substance in the melt liquid prepared in step 2) to obtain an injection melt liquid kept warmed at 50 to 90° C.; and 4) injecting such injection melt liquid into air by means of an injection-type granulator, being followed by freezing and solidifying.

As for a method of obtaining an injection melt liquid, on the other hand, while a method can be considered of simultaneously dissolving all the raw materials including a biologically active substance at 50 to 90° C. to obtain an injection melt liquid, an important factor to be pointed out is that the injection melt liquid should be prepared by keeping the melt liquid including the biologically active substance at temperature not exceeding 90° C., or alternatively by minimizing duration time at temperature above 90° C. It is because the biologically active substance is prone to be disintegrated at temperature exceeding 90° C., making it difficult, if not possible, to obtain a prescribed content value in the obtained rumen bypass product. Especially in the case of a thermally vulnerable biologically active substance being included, the granulation through injection which can be practiced at lower temperature is extremely useful. A method such as granulation through extrusion, in which a fabrication is inevitably carried out under elevated temperature and pressure, has the disadvantage that a thermally vulnerable biologically active substance is inapplicable, while the granulation through injection in accordance with the present embodiment renders it possible to granulate at lower temperature, so that this method can be applied to a rumen bypass product containing such a thermally vulnerable biologically active substance. It is to be noted that the melting temperature for the spray melt blending liquid should be set preferably at 50 to 90° C., more preferably at 60° C. to 75° C.

Also, the granulation through injection in accordance with the present embodiment has an advantage that a rumen bypass product can be easily obtained at a lower cost because a melt liquid of the coating composition is blended with the biologically active substance for granulating through injecting into air, which process requires a much smaller number of manufacturing steps when compared with granulation through extrusion. In particular, the granulation through extrusion has many complicated manufacturing steps involved, calling for an expensive apparatus, whereas the granulation through injection does not require such an expensive apparatus, resulting in a less expensive cost of manufacture. Furthermore, the biologically active substance can be dispersed by injection uniformly in the coating composition to obtain a rumen bypass product in a spherical form and with a sorted particle size. As such, the fabrication method in accordance with the present embodiment is extremely advantageous in that a high quality rumen bypass product can be fabricated in a very easy and inexpensive manner.

The injection into air has further been found to be a manufacturing method with a lower cost of manufacture because a much smaller number of manufacturing steps are involved; the injection method does not require a step of drying water or removing oil after granulation, which is inherent to a method of cooling and solidifying in water or oil. Particularly, in granulating through injecting into air the injection melt liquid which has a biologically active substance and a preservative dispersed and/or molten in a melt blending liquid, a rumen bypass product in a spherical form is easily obtained through a granulation process alone, at a lower cost of manufacture. Since the rumen bypass product is prepared particularly in a spherical form, the surface of the biologically active substance can be free from a jut such as an edge, being uniformly coated with a coating composition. Such uniformly coated rumen bypass product can accomplish a stable protective function with a lesser amount of elution within the rumen. In addition, by virtue of a smooth surface without an edge, the coating composition will not be abraded and peeled off in the ruminal inner wall, which advantageously ensures that the protective function for the biologically active substance is performed.

For allowing the biologically active substance to be released in the abomasum and/or the subsequent digestive tract, lecithin may suitably be contained in the rumen bypass product. The lecithin works well as a release controller in the abomasum and/or the subsequent digestive tract. Further, by adding a stearic acid, a rumen bypass product can be obtained which is excellent in protective ability in the rumen and releasability in the abomasum and/or the subsequent digestive tract.

(Particle Size)

When a feed additive composition for ruminants is prepared into a rumen bypass product, the preparation should be in a spherical form with a mean particle size of 0.1 mm to 3.0 mm, preferably 0.5 mm to 2.0 mm. The smaller the preparation's particle size, the shorter the residence time in the rumen, resultantly with better digestion. Accordingly, the particle size is preferably 0.5 mm to 1.5 mm.

As for a particle size of the biologically active substance, a smaller size will reduce the amount of biologically active substance present on or near the surface of the spherical rumen bypass product, which renders a coating easier. Accordingly, a finer powder is preferably employed.

A means to obtain a fine powder of biologically active substance includes a pulverization using a pin-type mill, a ball mill, or a jet mill, so that a suitable rumen bypass product may be prepared by limiting a mean particle size to less than 150 μm. On the other hand, if a biologically active substance pulverized to a mean particle size of less than 1 μm is dispersed in a melt blending liquid, an injection will become difficult due to a correspondingly increased viscosity of the injection melt liquid, which will resultantly necessitate considerably reducing a content of biologically active substance. On the other hand, if a mean particle size is larger than 150 μm, it will become difficult to fully coat the surface of the biologically active substance with the coating composition, which will thus lead to a partial exposure. As such, it is required that a mean particle size of the biologically active substance be controlled between 1 and 150 μm. The size range is preferably 10 to 150 μm, more preferably 50 to 150 μm.

(Biologically Active Substance)

In the present embodiment, a biologically active substance includes various known nutrient materials and feed containing such nutrient materials, or medicaments, for example, amino acids, vitamins, enzymes, proteins, carbohydrates, natural substances, and medicines, which are selected individually or in a mixture of two or more.

To be more specific, the biologically active substance will include:

a member of amino acids, such as aminoacetic acid, alanine, arginine, lysine (lysine hydrochlorides etc.), sodium glutamate, methionine, tryptophane, threonine, valine, betaine, taurine, etc., which belong to amino acids and/or their derivatives;

a member of vitamins, such as vitamin C, vitamin BI, vitamin B2, vitamin B6, vitamin B12, choline chloride, calcium pantothenate, nicotinic acid, nicotinic acid amide, biotin, folic acid, p-aminobenzoic acid, etc., which belong to water-soluble vitamins and/or other substances having corresponding functions;

a member of enzymes, such as protease, amylase, lipase, mixed enzymes, etc.; a member of proteins, such as casein, corn protein, etc.;

a member of carbohydrates, such as starch, sucrose, dextrose, etc;

a member of natural products, such as fish meal, kelp meal, blood meal, grain flour, bile powder, etc.;

a member of medicaments, such as antibiotic drug, hormone drug, etc.;

the antibiotic drug further including kanamycin sulfate etc. as a member of aminoglycosides; vancomycin etc. as a member of glycopeptides; oxytetracycline etc. as a member of tetracyclines; ampicillin etc. as a member of penicillins; erythromycin etc. as a member of macrolides; lincomycin etc. as a member of lincomycins; a chloramphenicol group; a phosphomycin group etc.;

the hormone drug further including estrogen, stilbestrol, hexestrol, etc.

Furthermore, a content of the biologically active substance is selected in a range of 1 to 50% by weight, preferably 20 to 50% by weight, more preferably 30 to 45% by weight. In particular, since an increased content of water-soluble biologically active substance will yield a higher viscosity, injection will become difficult in granulation through injection.

In order to meet a demand that a more portion of biologically active substance be contained in a rumen bypass product, the content of biologically active substance should be determined, aiming at a suitable balance.

It is also possible to suitably contain a fat-soluble vitamin such as vitamin A, vitamin D, vitamin E, etc.

In a coating composition which serves as a coating agent for coating the biologically active substance, on the other hand, its specific gravity may be adjusted, if desired, by adding a specific gravity controller such as a calcium carbonate, talc, etc.

To produce a protective material, a member of hardened animal fats can be employed, such as beef tallow, lard, etc.; and a member of hardened vegetable oils can be employed, such as a hardened palm oil, a hardened soybean oil, a hardened rapeseed oil, a hardened castor oil, etc. Available as a member of linear or branched, saturated or unsaturated aliphatic monocarboxylic acids having 12 to 22 carbon atoms are such as a lauric acid, a myristic acid, a palmitic acid, a stearic acid, an oleic acid, a linolic acid, etc. Available as a member of fatty acid esters are such as a monoester or diester of a saturated or unsaturated fatty acid in combination with glycerin, as exemplified by a glycerine fatty acid ester, a sucrose fatty acid ester, etc. Available as a member of wax group are such as a carnauba wax, a bees wax, a natural wax, a synthetic wax, a paraffin wax, etc., being selected individually or in a mixture of two or more. An amount of use is selected in a range of 20 to 98% by weight, preferably 30 to 90% by weight.

Available as a member of linear or branched, saturated or unsaturated aliphatic monocarboxylic acids having 12 to 22 carbon atoms and their salts are such as a myristic acid, a palmitic acid, a stearic acid, an oleic acid, a linolic acid, a behenic acid or their salts, being selected individually or in a mixture of two or more. The amount of use is selected in a range of 0.1 to 50% by weight, preferably 1 to 40% by weight. Further, the lecithin in the coating composition is selected in a range of 0.1 to 10% by weight, preferably 0.5 to 7% by weight, more preferably 0.5 to 5.0% by weight.

(Preservative Agent)

A preservative agent serves to inhibit a growth of mold, bacteria, etc. or exhibits an antibacterial action, and an antifungal agent etc. can be employed for such purposes. When contained in a rumen bypass product, the preservative is believed to minimize attack and breakdown of a biologically active substance by rumen microorganisms as well as intrusion in the vicinity of the surface of the rumen bypass product, resultantly working to prevent a disintegration. Particularly, when the preservative is blended and dispersed in a coating composition which coats the biologically active substance, such preservative can efficiently perform its preservative function without damaging the biologically active substance. As for an amount of the preservative to be added, an excessive addition is likely to affect microbial propagation and growth, while an insufficient addition may defeat an expected effect. Thus, the content of preservative should desirably be 0.01 to 2.0% by weight, preferably 0.1 to 1.0% by weight, based on a total amount of the rumen bypass product. The preservative is preferably in the form of a fine powder. Also, it is desirable that the preservative be pulverized for use, as may be needed. It is also possible to improve a rumen bypass ratio by 10 to 50% when the preservative is dispersed in the coating composition so that attack by the rumen microorganisms may be inhibited.

Available as a preservative agent is a blend of at least one selected from the group consisting of a propionic acid or its salt, a sorbic acid or its salt, a benzoic acid or its salt, a dehydroacetic acid or its salt, parahydroxybenzoic esters, an imazalil, a thiabendazole, an orthophenyl phenol, an orthophenyl phenol natrium, and a diphenyl. Available here as a member of propionic acids or their salts are a propionic acid, a calcium propionate, a sodium propionate, etc. Also available as a member of sorbic acids or their salts are a sorbic acid, a potassium sorbate, etc.; available as a member of benzoid acids and their salts are such as a benzoic acid, a sodium benzoate, etc.; available as a member of dehydroacetic acids or their salts are such as a dehydroacetic acid, a sodium dehydroacetate, etc.; available as a member of parahydroxybenzoic esters are an isobutyl parahydroxybenzoate, an isopropyl parahydroxybenzoate, an ethyl parahydroxybenzoate, a butyl parahydroxybenzoate, a propyl parahydroxybenzoate, etc.

Furthermore, a rumen bypass product obtained by granulation through injection can be prepared into feed when uniformly blended, by means of a blender such as a ribbon mixer etc., with other materials such as defatted rice bran, wheat flour, dehydrated bean curd refuse, corn flour and/or fish meal.

Example 1

While various examples shall be enumerated below with a detailed description, the present invention is, in no way, limited to such examples.
(Preparation of the Rumen Bypass Product)

A melt liquid of coating composition was prepared, first by measuring 1200 g of methionine, 1650 g of hardened rapeseed oil, 50 g of lecithin, 70 g of stearic acid, and 30 g of palmitic acid, and then by heating a mixture of hardened rapeseed oil, lecithin, and stearic acid at 85° C. The methionine was uniformly blended and dispersed in such melt liquid of coating composition to produce an injection melt liquid being kept warmed at 85° C. The injection melt liquid was injected into air to obtain a rumen bypass product solidified into a spherical form of 0.1 to 3 mm diameter. The rumen bypass product was assayed in the following method.
(Evaluation of Protective Ability in the Rumen)

The rumen bypass product was immersed in McDougall's buffer corresponding to the ruminal fluid, and was shaken for 16 hours. After completion of the shaking, a released amount of the particular ingredient was assayed, in ratio to the amount of the total biologically active substance. The McDougall's buffer is a solution prepared by dissolving 7.43 g of sodium hydrogencarbonate, 7.00 g of disodium phosphate 12 hydrate, 0.34 g of sodium chloride, 0.43 g of potassium chloride, 0.10 g of magnesium chloride 6 hydrate, and 0.05 g of calcium chloride in 1000 mL of water.
(Evaluation of Releasability in the Abomasum)

After the release ratio in the rumen was determined, solid matter was filtrated out, and was immersed in Clark-Lubs's buffer corresponding to the abomasal fluid, followed by shaking for 2 hours. After completion of the shaking, the released amount of the particular ingredient was assayed, in ratio to the amount of the total biologically active substance. The Clark-Lubs's buffer is a solution prepared by dissolving 3.73 g of potassium chloride and 2.1 mL of hydrochloride acid in 1000 mL of water.
(Evaluation of Releasability in the Small Intestine)

After the release ratio in the abomasum was determined, solid matter was filtrated out, and was immersed in a buffer corresponding to the small-intestinal fluid, followed by shaking for 7 hours. After completion of the shaking, the released amount of the particular ingredient was assayed, in ratio to the amount of the total biologically active substance.

The above-described evaluations on this rumen bypass product revealed the result that a release ratio was 2% in the rumen, 23% in the abomasum, and 71% in the small intestine.

Example 2

Next, another rumen bypass product is prepared in accordance with Example 2 of the present invention. A melt liquid of coating composition was prepared, first by measuring 1200 g of lysine hydrochloride, 1300 g of hardened rapeseed oil, 30 g of lecithin, and 470 g of stearic acid, and then by melting the hardened rapeseed oil, followed by adding the lecithin and the stearic acid to be kept warmed at 80° C. The lysine hydrochloride was uniformly blended and dispersed in such melt liquid of coating composition to produce an injection melt liquid being kept warmed at 80° C. The injection melt liquid was injected into air to obtain a rumen bypass product solidified into a spherical form of 0.1 to 3 mm diameter. The rumen bypass product in Example 2 was assayed in the same method as was employed in Example 1. The evaluation result is illustrated in Table 1.

Example 3

Yet another rumen bypass product was prepared in accordance with Example 3 of the present invention. A melt liquid of coating composition was prepared, first by measuring 150 g of lysine hydrochloride, 400 g of methionine, 10 g of vitamin B1, 1750 g of hardened rapeseed oil, 300 g of hardened palm oil, 90 g of lecithin, and 300 g of stearic acid, and then by melting the hardened rapeseed oil and the hardened palm oil, followed by adding the lecithin and the stearic acid to be kept warmed at 75° C. The lysine hydrochloride, the methionine, and the vitamin B1 were uniformly blended and dispersed in such melt liquid of coating composition to produce an injection melt liquid being kept warmed at 75° C. The injection melt liquid was injected into air to obtain a rumen bypass product solidified into a spherical form of 0.1 to 3 mm diameter. The rumen bypass product in Example 3 was assayed in the same method as was employed in Example 1. The evaluation result is likewise illustrated in Table 1.

Example 4

Still another rumen bypass product was prepared in accordance with Example 4 of the present invention. A melt liquid of coating composition was prepared, first by measuring 150 g of lysine hydrochloride, 150 g of methionine, 200 g of betaine, 50 g of nicotinic acid, 100 g of taurine, 2150 g of hardened palm oil, 50 g of lecithin, and 150 g of stearic acid, and then by heating a mixture of the hardened palm oil, the lecithin, and the stearic acid to be kept warmed at 70° C. The lysine hydrochloride, methionine, betaine, nicotinic acid and taurine were uniformly blended and dispersed in such melt liquid of coating composition to produce an injection melt liquid being kept warmed at 70° C. The injection melt liquid was injected into air to obtain a rumen bypass product solidified in a spherical form of 0.1 to 3 mm diameter. The rumen bypass product in Example 4 was assayed in the same method as was employed in Example 1. The evaluation result is also illustrated in Table 1.

Comparative Example 1

Next, by way of Comparative Example 1, a commercially available rumen bypass product was subjected to the same evaluation method as was employed in Example 1, and the evaluation result is also illustrated in Table 1.

TABLE 1

| | Release Ratio of Biologically Active Substance (%) | | | |
|---|---|---|---|---|
| | in Simulated Ruminal | | in Simulated Abomasal and Postabomasal Fluids (Abomasal Fluid + Small Intestinal Fluid) | |
| Example and Comparative Example | Biologically Active Substance | Release Ratio | Biologically Active Substance | Release Ratio |
| Example 1 | Methionine | 2% | Methionine | 94% |
| Example 2 | Lysine | 9% | Lysine | 81% |
| Example 3-1 | Methionine | 6% | Methionine | 91% |
| Example 3-2 | Lysine | 12% | Lysine | 87% |
| Example 3-3 | Vitamin B1 | 14% | Vitamin B1 | 81% |
| Example 4-1 | Methionine | 8% | Methionine | 92% |
| Example 4-2 | Lysine | 16% | Lysine | 82% |
| Example 4-3 | Nicotinic Acid | 14% | Nicotinic Acid | 83% |
| Example 4-4 | Betaine | 16% | Betaine | 81% |
| Example 4-5 | Taurine | 9% | Taurine | 85% |
| Comparative Example 1 | Lysine | 51% | Lysine | 44% |

Based on the rumen bypass products employed in Examples 1 to 4 and Comparative Example 1 as illustrated in Table 1, the release ratios both in the simulated ruminal fluid and in the simulated abomasal and postabomasal fluids are graphically represented in FIG. 1. In FIG. 1, a rumen bypass product exhibits its preferred characteristics when release ratio is lower in the simulated ruminal fluid and higher in the simulated abomasal and postabomasal fluids, that is, when the graphic line is ascendant toward the right hand side. As distinctly shown in Table 1 and FIG. 1, even when containing two or more water-soluble biologically active substances, the inventive rumen bypass product exhibited an excellent bypassing property in the simulated ruminal fluid of ruminants and an extremely excellent releasability in the simulated abomasal and postabomasal fluids.

To put it another way, when orally administered to ruminants, the inventive product has been found to be an extremely effective rumen bypass product, in that the rumen bypass product containing a multiplicity of biologically active substances with a higher water solubility bypasses the rumen and is released in the abomasum and/or the subsequent digestive tract, to be absorbed by ruminants without a loss. In addition, the present method of fabricating a rumen bypass substance ensures that a large contribution can be made to industries, especially to a livestock industry, in that a cost of manufacture and a cost of sales will be made extremely low because the rumen bypass product is produced only by a step of granulating a molten material which is dispersed in a coating composition where the biologically active substance is melt.

(Evaluation of the Rumen Bypass Product)

Next, an evaluation was made on the effects which the rumen bypass product is to be subjected to by microorganisms residing in the rumen of ruminants. The evaluation methods employed in Examples 5 to 9 and Comparative Examples 2 to 6 were in the following manner.

(Evaluation of Protective Ability in the Rumen)

A tube was inserted through the cattle's mouth to the middle level and nearly lower level of the rumen to suck up the ruminal fluid. After obtaining the ruminal fluid, a rumen bypass product was immediately immersed in 900 mL of the ruminal fluid and agitated at 40° C. for 16 hours. After completion of the agitation, the entire rumen bypass product provided in this experiment was recovered to determine and evaluate a residual ratio (a rumen bypass ratio) of the biologically active substance.

(Evaluation of Releasability in the Abomasum)

The rumen bypass product was immersed in 900 mL of the ruminal fluid obtained in the above-mentioned method, and was agitated at 40° C. for 16 hours. After completion of the agitation, the entire rumen bypass product provided in this experiment was recovered and immersed in 900 mL of the Clark-Lubs's buffer corresponding to the abomasal fluid. The released amount of biologically active substance was determined and evaluated after the fluid was agitated at 37° C. for 2 hours. Again, the Clark-Lubs's fluid is a solution prepared by dissolving 3.73 g of potassium chloride and 2.1 mL of hydrochloride acid in water.

(Evaluation of Releasability in the Small Intestine)

After the release ratio in the abomasum was determined, the entire rumen bypass product provided in this experiment was recovered and immersed in 900 mL of a buffer corresponding to the intestinal fluid. After shaking the fluid at 37° C. for 7 hours, the released amount of the biologically active substance was determined and evaluated.

Example 5

After 1626 g of hardened rapeseed oil, 90 g of lecithin, and 150 g of stearic acid were melt and blended, being kept warmed at 80° C., 1125 g of lysine hydrochloride with a sorted particle size (a mean particle size of approximately 50 μm) and 9 g of calcium propionate (a preservative) were added to such melt blending liquid and uniformly dispersed to produce an injection melt liquid. Such injection melt liquid was injected into air to obtain a rumen bypass product which is solidified into a spherical form of 0.5 to 2.0 mm diameter.

Example 6

After 1626 g of hardened rapeseed oil, 90 g of lecithin, and 150 g of stearic acid were melt and blended, being kept warmed at 80° C., 1125 g of lysine hydrochloride with a sorted particle size (a mean particle size of approximately 50 μm) and 9 g of sodium propionate (a preservative) were added to such melt blending liquid and uniformly dispersed to obtain a rumen bypass product produced in the same manner as in Example 5.

Example 7

After 1517 g of hardened palm oil, 90 g of lecithin, and 150 g of stearic acid were melt and blended, being kept warmed at 80° C., 1125 g of lysine hydrochloride with a sorted particle size (a mean particle size of approximately 50 μm), 18 g of calcium propionate (a preservative), and 100 g of calcium carbonate were added to such melt blending liquid and uniformly dispersed to obtain a rumen bypass product produced in the same manner as in Example 5.

Example 8

After 1608 g of hardened rapeseed oil, 90 g of lecithin, and 150 g of stearic acid were melt and blended, being kept warmed at 80° C., 1125 g of lysine hydrochloride with a sorted particle size (a mean particle size of approximately 50 μm) and 27 g of calcium propionate (a preservative) were added to such melt blending liquid and uniformly dispersed to obtain a rumen bypass product produced in the same manner as in Example 5.

Example 9

After 1517 g of hardened rapeseed oil, 90 g of lecithin, and 150 g of stearic acid were melt and blended, being kept warmed at 80° C., 1125 g of taurine with a sorted particle size (a mean particle size of approximately 50 μm), 18 g of calcium propionate (a preservative), and 100 g of calcium carbonate were added to such melt blending liquid and uniformly dispersed to obtain a rumen bypass product produced in the same manner as in Example 5.

Comparative Example 2

After 1635 g of hardened rapeseed oil, 90 g of lecithin, and 150 g of stearic acid were melt and blended, being kept warmed at 80° C., 1125 g of lysine hydrochloride with a sorted particle size (a mean particle size of approximately 50 μm) was added to such melt blending liquid and uniformly dispersed to obtain a rumen bypass product produced in the same manner as in Example 5.

Comparative Example 3

After 1535 g of hardened palm oil, 90 g of lecithin, and 150 g of stearic acid were melt and blended, being kept warmed at 80° C., 1125 g of lysine hydrochloride with a sorted particle size (a mean particle size of approximately 50 μm) and 100 g of calcium carbonate were added to such melt blending liquid and uniformly dispersed to obtain a rumen bypass product produced in the same manner as in Example 5.

Comparative Example 4

After 1716 g of hardened rapeseed oil and 150 g of stearic acid were melt and blended, being kept warmed at 80° C., 1125 g of lysine hydrochloride with a sorted particle size (a mean particle size of approximately 50 μm) and 9 g of calcium propionate (a preservative) were added to such melt blending liquid and uniformly dispersed to obtain a rumen bypass product produced in the same manner as in Example 5.

Comparative Example 5

After 1626 g of hardened rapeseed oil, 90 g of lecithin, and 150 g of stearic acid were melt and blended, being kept warmed at 80° C., 1125 g of lysine hydrochloride with a sorted particle size (a mean particle size of approximately 200 μm) and 9 g of calcium propionate (a preservative) were added to such melt blending liquid and uniformly dispersed to obtain a rumen bypass product produced in the same manner as in Example 5.

Comparative Example 6

After 1535 g of hardened rapeseed oil, 90 g of lecithin, and 150 g of stearic acid were melt and blended, being kept warmed at 80° C., 1125 g of taurine with a sorted particle size (a mean particle size of approximately 50 μm) and 100 g of calcium carbonate were added to such melt blending liquid and uniformly dispersed to obtain a rumen bypass product produced in the same manner as in Example 5.

Examples 5 to 9 are summarized in Table 2, and Comparative Examples 2 to 6 are summarized in Table 3. Further, based on a rumen bypass product in Examples 5 to 9 and Comparative Examples 2 to 6 which are respectively illustrated in Table 2 and Table 3, the release ratios both in the ruminal fluid and in the abomasal and intestinal fluids are graphically represented in FIG. 2. In FIG. 2 as well, a rumen bypass product exhibits its preferred characteristics when the graphic line is ascendant toward the right hand side. As can be seen in these illustrations, a rumen bypass product containing a preservative with an antifungal effect exhibits excellent results in protective ability (a rumen bypass ratio) in the rumen of ruminants.

ened animal fat, and a hardened vegetable oil, lecithin, and a preservative. Also, addition of the preservative is expected to improve a rumen bypass ratio by 10% to 50%.

TABLE 2

| | | | Example No | | | | |
|---|---|---|---|---|---|---|---|
| | | | 5 | 6 | 7 | 8 | 9 |
| Biologically Active Substance | | | Lysine hydro-chloride | Lysine hydro-chloride | Lysine hydro-chloride | Lysine hydro-chloride | Taurine |
| Mean Particle Size (μm: approx) | | | 50 | 50 | 50 | 50 | 50 |
| % by weight | | | 37.5 | 37.5 | 37.5 | 37.5 | 37.5 |
| Coating Composition (%) | A: Protective Material | Hardened Rapeseed Oil | 54.2 | 54.2 | | 53.6 | 50.6 |
| | | Hardened Palm Oil | | | 50.6 | | |
| | | Stearic Acid | 5.0 | 5.0 | 5.0 | 5.0 | 5.0 |
| | B: | Lecithin | 3.0 | 3.0 | 3.0 | 3.0 | 3.0 |
| | C: Preservative | Calcium Propionate | 0.3 | | 0.6 | 0.9 | 0.6 |
| | | Sodium Propionate | | 0.3 | | | |
| Calcium Carbonate (%) (Specific Gravity Controller) | | | | | 3.3 | | 3.3 |
| Release Ratio in the Rumen (%) | | | 16.8 | 15.3 | 20.4 | 9.8 | 11.9 |
| Rumen Bypass Ratio (%) | | | 83.2 | 84.7 | 79.6 | 90.2 | 88.1 |
| Release Ratio in the Simulated Abomasal and Postabomasal Fluids (Abomasal Fluid + Intestinal Fluid: %) | | | 78.7 | 78.9 | 79.5 | 89.9 | 87.0 |

TABLE 3

| | | | Comparative Example No | | | | |
|---|---|---|---|---|---|---|---|
| | | | 2 | 3 | 4 | 5 | 6 |
| Biologically Active Substance | | | Lysine hydro-chloride | Lysine hydro-chloride | Lysine hydro-chloride | Lysine hydro-chloride | Taurine |
| Mean Particle Size (μm: approx) | | | 50 | 50 | 50 | 200 | 50 |
| % by weight | | | 37.5 | 37.5 | 37.5 | 37.5 | 37.5 |
| Coating Composition (%) | A: Protective Material | Hardened Rapeseed Oil | 54.5 | | 57.2 | 54.2 | 51.2 |
| | | Hardened Palm Oil | | 51.2 | | | |
| | | Stearic Acid | 5.0 | 5.0 | 5.0 | 5.0 | 5.0 |
| | B: | Lecithin | 3.0 | 3.0 | | 3.0 | 3.0 |
| | C: Preservative | Calcium Propionate | | | 0.3 | 0.3 | |
| | | Sodium Propionate | | | | | |
| Calcium Carbonate (%) (Specific Gravity Controller) | | | | 3.3 | | | 3.3 |
| Release Ratio in the Rumen (%) | | | 43.9 | 54.5 | 22.7 | 57.9 | 33.6 |
| Rumen Bypass Ratio (%) | | | 56.1 | 45.5 | 77.3 | 42.1 | 66.4 |
| Release Ratio in the Simulated Abomasal and Postabomasal Fluids (Abomasal Fluid + Intestinal Fluid: %) | | | 55.2 | 45.4 | 39.2 | 41.7 | 65.3 |

As described above, it has been found that the rumen bypass product for ruminants, which has a biologically active substance coated with a coating composition, has an excellent protective ability (a high rumen bypass ratio) as well as excellent releasabilities in the abomasum and/or the subsequent digestive tract, the coating composition including: (A) at least one protective material selected from the group consisting of a hardened animal fat, a hardened vegetable oil, a linear or branched, saturated or unsaturated aliphatic monocarboxylic acid having 12 to 22 carbon atoms, a fatty acid ester, and a wax group; (B) lecithin; and (C) at least one preservative selected from a propionic acid or its salt, a sorbic acid or its salt, a benzoic acid or its salt, a dehydroacetic acid or its salt, parahydroxybenzoic acid esters, an imazalil, a thiabendazole, an orthophenyl phenol, an orthophenyl phenol natrium, and a diphenyl.

In this manner, a rumen bypass product for ruminants which has an excellent protective ability can be obtained by allowing a biologically active substance to be enclosed with a coating composition which contains a substance selected, individually or in a mixture of two or more, from the group consisting of a linear or branched, saturated or unsaturated monocarboxylic acid having 12 to 22 carbon atoms, a hard- Next, stability of the biologically active substance was studied in order to determine optimum temperature for the spray melt blending liquid used in the granulation through injection. Here, the spray melt blending liquid was prepared which contains vitamins, particularly, a calcium pantothenate, a nicotinic acid, and a methionine which are commonly available as a biologically active substance; the amounts of such contents were determined, being based on the rumen bypass product that was obtained by injecting after agitating the liquid, for 1 hours, at melting temperature being set at 60° C., 65° C., 70° C., 75° C., and 80° C. The result is shown in Table 4 and FIG. 3. Table 4 indicates that the calcium pantothenate, kept warmed at 80° C., has its content reduced, from which the content is estimated to be below 50% when kept warmed above 90° C. However, when kept warmed below 75° C., the content remains high. Based on this fact, in the case of a rumen bypass product with a biologically active substance, employing a thermally vulnerable vitamins such as a calcium pantothenate, such vitamins can be contained in the preparation without suffering from any damage when granulation through injection is carried out, limiting the temperature of spray melt blending liquid to less than 75° C.

TABLE 4

| Biologically Active Substance | Mean Content (%) Melting Temperature (° C.) | | | | |
|---|---|---|---|---|---|
| | 60 | 65 | 70 | 75 | 80 |
| Methionine | 100.5 | 100.3 | 103.6 | 104.2 | 109.6 |
| Calcium Pantothenate | 98.6 | 96.9 | 97.1 | 94.5 | 71.5 |
| Nicotinic Acid | 99.5 | 98.2 | 100.3 | 101.2 | 102.0 |

INDUSTRIAL APPLICABILITY

In accordance with the inventive feed additive composition for ruminants, the feed containing the same, and the method of fabricating the feed additive composition for ruminants, the rumen bypassing methionine type of amino acid, the rumen bypassing protein, and the like can be suitably employed as an additive for rumen bypassing feed.

Figure 1:
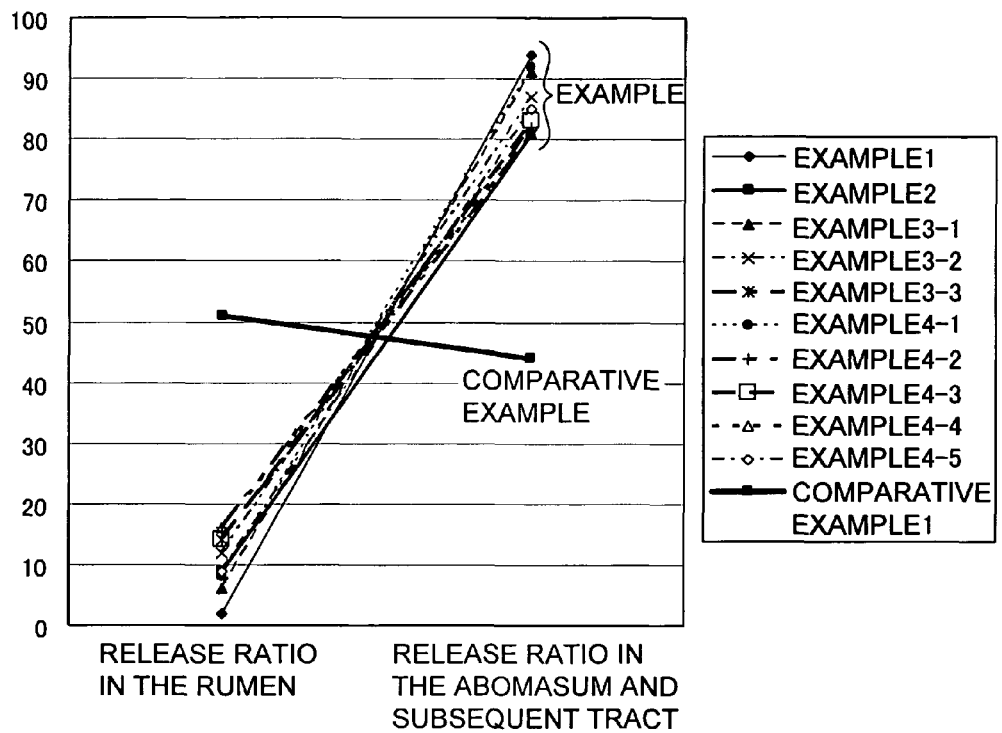
FIG. 1 is a graphical representation of the release ratios both in the simulated ruminal fluid and in the simulated abomasal and postabomasal fluids, based on the rumen bypass products in Examples 1 to 4 and Comparative Example 1.
Figure 2:
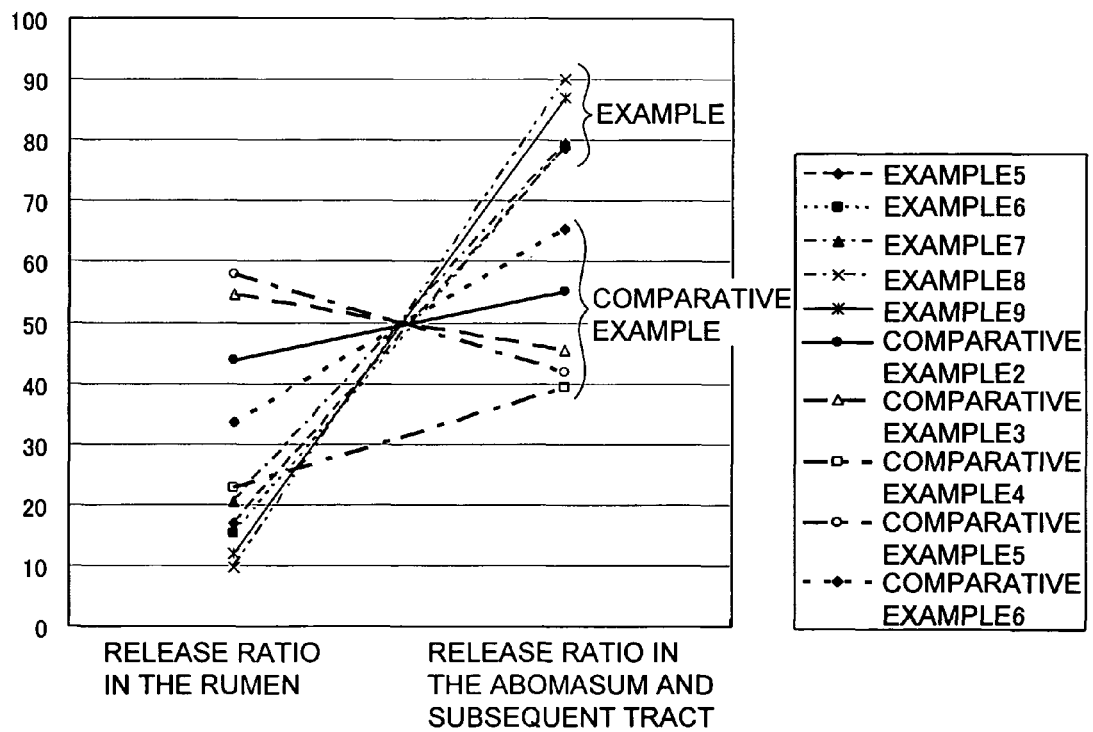
FIG. 2 is a graphical representation of the release ratios both in the ruminal fluid and in the abomasal and intestinal fluids, based on the rumen bypass products in Examples 5 to 9 and Comparative Examples 2 to 6.
Figure 3:
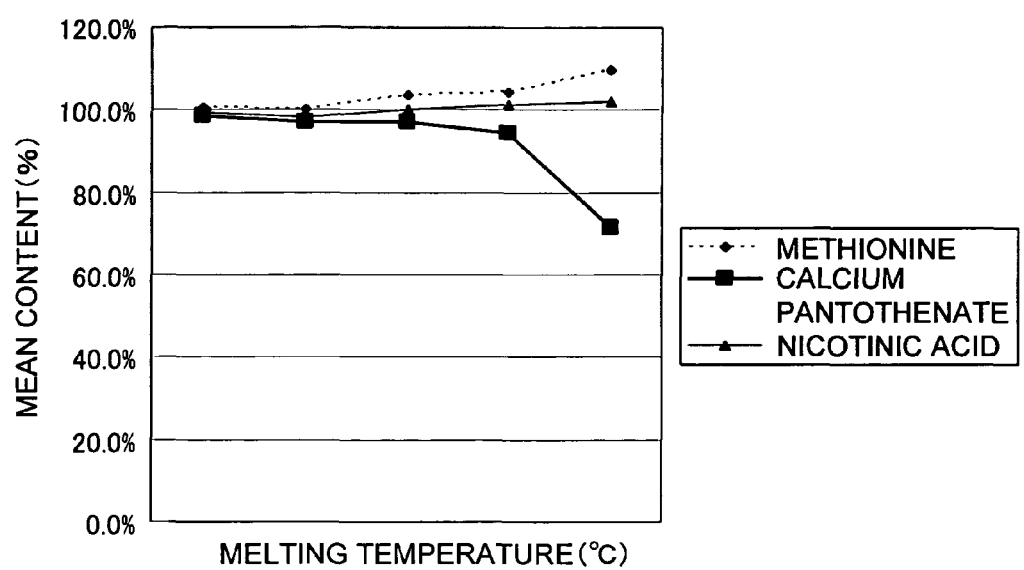
FIG. 3 is a graphical representation of a mean content of vitamins, based on each melting temperature.

The invention claimed is:

1. A feed additive composition for ruminants which has a biologically active substance coated with a coating composition,
   wherein the coating composition comprises:
      at least one protective material selected from the group consisting of a hardened animal fat, a hardened vegetable oil, a linear or branched, saturated or unsaturated aliphatic monocarboxylic acid having 12 to 22 carbon atoms, a fatty acid ester, and a wax group;
      lecithin; and
      at least one preservative selected from a propionic acid or a salt thereof, a sorbic acid or a salt thereof, a benzoic acid or a salt thereof, a dehydroacetic acid or a salt thereof, parahydroxybenzoic acid esters, an imazalil, a thiabendazole, an orthophenyl phenol, an orthophenyl phenol natrium, and a diphenyl, and
   wherein the preservative is dispersed only in the coating composition which coats the biologically active substance.

2. The feed additive composition for ruminants as recited in claim 1, wherein a content of the preservative is in a range of from 0.01 to 2.0% by weight.

3. The feed additive composition for ruminants as recited in claim 1, wherein the preservative is a propionic acid or a salt thereof.

4. The feed additive composition for ruminants as recited in claim 1, wherein the biologically active substance contains at least a lysine hydrochloride.

5. The feed additive composition for ruminants as recited in claim 1, wherein the protective material contains at least a linear or branched, saturated or unsaturated aliphatic monocarboxylic acid having 12 to 22 carbon atoms.

6. The feed additive composition for ruminants as recited in claim 1, wherein the linear or branched, saturated or unsaturated aliphatic monocarboxylic acid having 12 to 22 carbon atoms is a stearic acid.

7. The feed additive composition for ruminants as recited in claim 1, wherein a mean particle size of the biologically active substance is in a range of from 1 to 150 μm.

8. The feed additive composition for ruminants as recited in claim 1, wherein a content of the lecithin is in a range of from 0.1 to 10.0% by weight.

9. The feed additive composition for ruminants as recited in claim 1, wherein a content of the biologically active substance is in a range of from 1 to 50% by weight.

10. The feed additive composition for ruminants as recited in claim 1, wherein the feed additive composition is made by a granulated injection melt liquid injected into air for granulation, the injection melt liquid being a melt blending liquid constituting the coating composition in which the biologically active substance is dispersed and/or dissolved.

11. The feed additive composition for ruminants as recited in claim 10, wherein the feed additive composition for ruminants obtained by granulation through injection is in a spherical form.

12. Feed containing the feed additive composition for ruminants as recited in claim 1.

* * * * *